(12) United States Patent
Dasgupta et al.

(10) Patent No.: US 9,874,553 B2
(45) Date of Patent: Jan. 23, 2018

(54) TARGETED CHEMICAL HIGH-THROUGHPUT SCREENING METHOD

(75) Inventors: Ramanuj Dasgupta, New York, NY (US); Foster Gonsalves, Brooklyn, NY (US)

(73) Assignee: New York University, New York, NY (US)

( * ) Notice: Subject to any disclaimer, the term of this patent is extended or adjusted under 35 U.S.C. 154(b) by 720 days.

(21) Appl. No.: 12/998,004

(22) PCT Filed: Sep. 10, 2009

(86) PCT No.: PCT/US2009/005075
§ 371 (c)(1),
(2), (4) Date: Jun. 21, 2011

(87) PCT Pub. No.: WO2010/030355
PCT Pub. Date: Mar. 18, 2010

(65) Prior Publication Data
US 2011/0251103 A1 Oct. 13, 2011

Related U.S. Application Data

(60) Provisional application No. 61/191,723, filed on Sep. 10, 2008.

(51) Int. Cl.
  *G01N 33/50* (2006.01)
  *C12Q 1/68* (2006.01)

(52) U.S. Cl.
  CPC ....... *G01N 33/5041* (2013.01); *C12Q 1/6897* (2013.01)

(58) Field of Classification Search
None
See application file for complete search history.

(56) References Cited

U.S. PATENT DOCUMENTS

| | | | |
|---|---|---|---|
| 2005/0256076 A1 | 11/2005 | Bumcrot | |
| 2006/0165699 A1 | 7/2006 | Colland et al. | |
| 2010/0267626 A1* | 10/2010 | Cheung et al. | 514/4.8 |
| 2011/0251144 A1 | 10/2011 | Moon et al. | |
| 2012/0264744 A1* | 10/2012 | Dasgupta et al. | 514/217.1 |

OTHER PUBLICATIONS

DasGuptal et al. Functional genomic analysis of the Wnt-wingless signaling pathway. Science. May 6, 2005;308(5723):826-33. Epub Apr. 7, 2005.*

Clemens et al., "Use of double-stranded RNA interference in Drosophila cell lines to dissect signal transduction pathways", Proceedings of National Academy of Sciences of the USA, 2000, vol. 97, No. 12, pp. 6499-6503.
Perrimon et al., "Drug-target identification in Drosophila cells: combining high-throughout RNAi and small-molecule screens", Drug Discovery Today, 2007, vol. 12, No. 1/2, pp. 28-33.
Eggert et al., "Parallel chemical genetic and genome-wide RNAi-screens identify cytokinesis inhibitors and targets", PLOS Biology, 2004, vol. 2, No. 12, pp. 2135-2143.
Kleino et al., "Pirk is a negative regulator of the Drosophila Imd Pathway", The Journal of Immunology, 2008, vol. 180, No. 8, pp. 5413-5422.
Barker et al., "Mining the Wnt pathway for cancer therapeutics", Nature Reviews, 2006, vol. 5, pp. 997-1014.
Luu et al., "Wnt/beta-catenin signaling pathway as novel cancer drug targets", Current Cancer Drug Targets, 2004, vol. 4, pp. 653-671.
Dasgupta et al., "High-throughput RNAi screen in Drosophila", In Wnt Signaling, vol. II: Pathway Models (ed. E. Vincan), 2008, vol. 469, pp. 163-184.
Lepourcelet et al., "Small-molecule antagonists of the oncogenic Tcf/beta-catenin protein complex", Cancer Cell, 2004, vol. 5, pp. 91-102.
Bejsovec, "Flying at the head of the pack: Wnt biology in Drosophila", Oncogene, 2006, 25:7442-7449.
Gonsalves et al., "An RNAi-based chemical genetic screen identifies three small-molecule inhibitors of the Wnt/wingless signaling pathway", PNAS, 2011, 108:5954-5963.

* cited by examiner

*Primary Examiner* — Nancy Treptow
(74) *Attorney, Agent, or Firm* — Mauriel Kapouytian Woods LLP; J. David Smith

(57) ABSTRACT

A novel method which integrates a "sensitized" chemical genetic high-throughput screen (HTS) with RNA interference (RNAi) screening technology is described herein. The present inventors used this method to identify specific small molecule inhibitors and activators of the Wnt pathway. More particularly, the screening method of the present invention may be used to identify small molecule inhibitors and activators that specifically target the activity of a stabilized pool of β-catenin. A number of compounds identified using the instant method, are shown herein to be small molecule inhibitors of the Wnt pathway that specifically target the activity of the stabilized pool of β-cat. The inhibitors identified by the present method may be prepared as pharmaceutical compositions, and may be used for the prevention and treatment of a variety of conditions in mammals including humans, including by way of non-limiting example, cancer, and others.

10 Claims, 8 Drawing Sheets

TARGETED CHEMICAL HIGH-THROUGHPUT SCREENING METHOD

CROSS REFERENCE TO RELATED APPLICATIONS

The present application is a National Stage Application claiming the priority of co-pending PCT Application No. PCT/US2009/005075 filed Sep. 10, 2009, which in turn, claims priority from U.S. Provisional Application No. 61/191,723, filed Sep. 10, 2008. Applicants claim the benefits of 35 U.S.C. § 120 as to the PCT application and priority under 35 U.S.C. § 119 as to the said United States Provisional application, and the entire disclosures of both applications are incorporated herein by reference in their entireties.

GOVERNMENT RIGHTS

This invention was made with government support under Grant No. W81XWH-04-1-0460 awarded by the Department of Defense. Accordingly, the United States Government has certain rights in the invention.

FIELD OF THE INVENTION

The present invention relates to a novel method which integrates a chemical high-throughput screen (HTS) with RNA interference (RNAi)-technology. This method enables the identification of specific small molecule modulators/modifiers of an RNAi-mediated loss-of-function (LOF) phenotype of genes that belong to known signaling pathways, thus resulting in the discovery of chemical agonists or antagonists of conserved cell signaling pathways. The utility of the present method is demonstrated by the identification of small molecule modulators that are capable of modulating the Wnt/wingless (wg) signaling pathway.

BACKGROUND OF THE INVENTION

Wnts/wg are a family of conserved signaling molecules that have been shown to regulate a plethora of fundamental developmental and cell biological processes, including cell proliferation, differentiation and cell polarity [Miller et al. Oncogene 18, 7860-72 (1999); Polakis. Genes Dev 14, 1837-51 (2000); Wodarz et al. Annu Rev Cell Dev Biol 14, 59-88 (1998)]. Mutations in the Wnt genes or in those genes encoding regulators of the Wnt/wg signaling pathway can cause devastating birth defects, including debilitating abnormalities of the central nervous system, axial skeleton, limbs, and occasionally other organs [Ciruna et al. Nature 439, 220-4 (2006); Grove et al. Development 125, 2315-25 (1998); Jiang et al. Dev Dyn 235, 1152-66 (2006); Kokubu et al. Development 131, 5469-80 (2004); Miyoshi et al. Breast Cancer Res 5, 63-8 (2003); Shu et al. Development 129, 4831-42 (2002); Staal et al. Hematol J 1, 3-6 (2000)]. Aberrant Wnt signaling has also been linked to human disease, such as hepatic, colorectal, breast and skin cancers [Miyoshi et al. supra (2003); Miyoshi et al. Oncogene 21, 5548-56 (2002); Moon et al. Nat Rev Genet 5, 691-701 (2004)].

Wnts/wg encode secreted glycoproteins that activate receptor-mediated pathways leading to numerous transcriptional and cellular responses [Wodarz et al. supra (1998); Moon et al. supra (2004); Nusse. Trends Genet 15, 1-3 (1999)]. The main function of the canonical Wnt pathway is to stabilize the cytoplasmic pool of a key mediator, β-catenin (β-cat)/armadillo (arm), which is otherwise degraded by the proteosome pathway (See FIG. 1). Initially identified as a key player in stabilizing cell-cell adherens junctions, β-cat/arm is also known to act as a transcription factor by forming a complex with the LEF/TCF (Lymphoid Enhancer Factor/T Cell Factor) family of HMG-box (High mobility group) transcription factors. Upon Wnt stimulation, stabilized β-cat/arm translocates to the nucleus, wherein together with LEF/TCF transcription factors, it activates downstream target genes [Miller et al. supra (1999); Staal et al. supra (2000); Nusse. supra (1999); Schweizer et al. Proc Natl Acad Sci USA 100, 5846-51 (2003)]. Catenin responsive transcription (CRT), which is the activation of transcriptional targets of β-cat, has been shown to regulate many aspects of cell growth, proliferation, differentiation and death. The Wnt/wg pathway can also be activated by inhibiting negative regulators such as GSK-3β (Glycogen Synthase Kinase-3β), APC (Adenomatous Polyposis Coli) and Axin that promote β-cat/arm degradation, or by introducing activating mutations in β-cat that render it incapable of interacting with the degradation complex, thus stabilizing its cytosolic pool [Logan et al. Annu Rev Cell Dev Biol 20, 781-810 (2004); Nusse et al. Cell Res 15, 28-32 (2005)]. Wnt/wg signaling can also activate an alternative "non-canonical" pathway that may lead to PKC (Protein Kinase C) and JNK (c-Jun N-terminal Kinase) activation resulting in calcium release and cytoskeletal rearrangements [Miller et al. supra (1999)].

At the plasma membrane, Wnt proteins bind to their receptor, belonging to the Frizzled family of proteins and the co-receptor encoded by LDL-related-protein-5, 6 (LRP5, LRP6)/arrow (arr, in *Drosophila*) [Schweizer et al. BMC Cell Biol 4, 4 (2003); Tamai et al. Mol Cell 13, 149-56 (2004)]. In the absence of the Wnt stimulus, GSK-3β is known to phosphorylate β-cat/arm, which marks it for ubiquitination and subsequent proteosome-mediated degradation. Activation of the receptor/co-receptor complex upon Wnt binding initiates a signal transduction cascade, which results in phosphorylation and subsequent inactivation of GSK-3β24.

Recent evidence has uncovered a new branch in the canonical Wnt/wg pathway whereby β-cat/arm can be stabilized in a GSK-3β independent fashion suggesting that regulated degradation of β-cat/arm (by GSK-3β) is not necessary for Wnt/wg signaling [Tolwinski et al. Dev Cell 4, 407-18 (2003); Tolwinski et al. Trends Genet 20, 177-81 (2004)]. Specifically, upon Wg binding, Arr directly recruits Axin (a scaffold protein which acts as a negative regulator) to the plasma membrane and causes its degradation. As a consequence, Arm no longer binds Axin or the degradation complex, resulting in nuclear accumulation and signaling by β-cat/Arm42.

In view of the above, a need exists for therapeutic agents, and corresponding pharmaceutical compositions and related methods of treatment that address conditions causally related to aberrant Wnt pathway activity and CRT activity, and it is toward the fulfillment and satisfaction of that need, that the present invention is directed.

SUMMARY OF THE INVENTION

As described herein for the first time, the present inventors have devised a novel method that combines the specificity of an RNAi-mediated phenotype created by a targeted RNAi "knock out" with a small molecule HTS. The present method can, therefore, be used advantageously to identify chemical compounds that specifically modulate (e.g., augment or reduce) the RNAi-mediated phenotype. As a consequence, the method of the present invention can pinpoint a particular target or juncture in a signaling pathway whose activity is modulated by a small molecule identified in the screen. This feature of the present method confers a specificity to the instant screen that does not exist in small molecule screens described to date, which broadly target whole signaling pathways, but do not delineate at which step in the pathway the small molecule acts. Accordingly, a small molecule identified using a standard small molecule HTS may affect a signaling pathway at multiple steps in the signaling cascade or may affect multiple signaling pathways. Identification of the particular target of a small molecule so identified requires additional analyses. In contrast, the present method provides a directed method that delineates small molecule targets in a single HTS.

The approach of combining genome-wide RNAi and small-molecule screens to drug-target identification should be widely applicable, both in *Drosophila* and in mammalian cells where there have been major advances in recent years in cell-based RNAi HTS. In addition to the direct (phenotypic) comparison approach, which has been previously utilized, the strategy of the present inventors is likely to be useful in drug discovery in "modifier" screens whereby cells are 'mutated' (or sensitized) by RNAi and screened for small molecules that modify the RNAi-induced phenotype. Such combination screens have the potential to identify very specific, active small molecules. Conversely, screens for RNAi modifiers of small molecule-induced phenotypes will also be valuable and applicable to many conserved cell signaling pathways, including the Sonic Hedgehog (SHH) pathway, Epidermal Growth Factor Receptor (EGFR)/Receptor Tyrosine Kinase (RTK) pathway, Notch pathway, Transforming Growth Factor (TGF-β)/Decepentaplegic (Dpp) pathway and the Janus Kinase (JAK)/Signal Transducers and Activator of Transcription (STAT) signaling pathway.

In accordance with the present invention, the inventors employed a novel methodology of integrating a "sensitized" chemical genetic high-throughput screen (HTS) with RNA interference (RNAi) screening technology in order to identify specific small molecule inhibitors of the Wnt pathway in *Drosophila* cells. As presented herein, this primary screening approach was used to identify small molecule modulators (inhibitors and activators) that specifically target the activity of the stabilized pool of β-cat. Experiments have also been performed to investigate the molecular mechanism(s) by which the candidate small molecules impact the activity of stabilized β-cat and identify their protein targets. The comprehensive approach of the present invention, which integrates small molecule screening with RNAi technology, has thus identified molecular tools useful for regulating the activity of the Wnt/β-catenin signaling pathway in normal and cancerous cells. The Examples presented herein, therefore, present clear proof of principle that the novel method of the present invention can be used advantageously to identify small molecules capable of modulating the activity of a particular component of a signaling pathway with exquisite specificity.

In accordance with the present invention, a method is presented for screening to identify an agent capable of modulating the activity of a signaling pathway in a cell, the method comprising:

a) contacting a plurality of cells in vitro with a double-stranded RNA (dsRNA) to induce uptake of the dsRNA into the plurality of cells, wherein the dsRNA is specific for a negative regulator of the signaling pathway and wherein uptake of the dsRNA reduces the activity of the negative regulator and thereby activates the signaling pathway in the plurality of cells; and b) dividing the plurality of cells comprising the activated signaling pathway into isolated subpopulations and incubating each isolated subpopulation in the presence of an agent to determine if the agent modulates the activity of the activated signaling pathway relative to a control agent, wherein each subpopulation is incubated with a different agent, and wherein an ability to modulate the activity of the activated signaling pathway relative to a control agent identifies the agent as capable of modulating the signaling pathway in a cell.

In accordance with another aspect of the invention, a method is presented for screening to identify an agent capable of modulating an RNA-interference (RNAi)-mediated phenotype in a cell, the method comprising:

a) contacting a plurality of cells in vitro with a double-stranded RNA (dsRNA) to induce uptake of the dsRNA into the plurality of cells, wherein the dsRNA is specific for a negative regulator of a signaling pathway and wherein uptake of the dsRNA reduces the activity of the negative regulator, thereby creating an RNAi-mediated phenotype characterized by activation of the signaling pathway in the plurality of cells; and b) dividing the plurality of cells having the RNAi-mediated phenotype into isolated subpopulations and incubating each isolated subpopulation in the presence of an agent to determine if the agent modulates the RNAi-mediated phenotype relative to a control agent, wherein each isolated subpopulation is incubated with a different agent, and wherein an ability to modulate the RNAi-mediated phenotype relative to the control agent identifies the agent as capable of modulating the RNAi-mediated phenotype in a cell.

In accordance with yet another aspect of the invention, a method is presented for screening to identify an agent capable of modulating the activity of a signaling pathway in a cell, the method comprising:

a) providing a plurality of cells in vitro, wherein the plurality of cells overexpresses a positive regulator of the signaling pathway and thereby activates the signaling pathway in the plurality of cells; and b) dividing the plurality of cells comprising the activated signaling pathway into isolated subpopulations and incubating each isolated subpopulation in the presence of an agent to determine if the agent modulates the activity of the activated signaling pathway relative to a control agent, wherein each subpopulation is incubated with a different agent, and wherein an ability to modulate the activity of the activated signaling pathway relative to a control agent identifies the agent as capable of modulating the signaling pathway in a cell.

As described herein, the present method may be a high throughput screen.

In an aspect of the invention, the method is performed in *Drosophila* cells, including primary *Drosophila* cells or *Drosophila* cell lines. In a particular embodiment of the invention, the *Drosophila* cell line is a Clone 8 cell lines or derivative thereof.

In yet another aspect of the invention, the signaling pathway is a conserved signaling pathway which is conserved among *Drosophila* and mammals. Exemplary conserved signaling pathways include the Wnt/wg signaling pathway, Sonic Hedgehog (SHH) pathway, Epidermal Growth Factor Receptor (EGFR)/Receptor Tyrosine Kinase (RTK) pathway, Notch pathway, Transforming Growth Factor (TGF-β)/Decepentaplegic (Dpp) pathway and the Janus Kinase (JAK)/Signal Transducers and Activator of Transcription (STAT) signaling pathway.

Negative regulators of such conserved signaling pathways include axin, Glycogen Synthase Kinase-3β (GSK-3β), Adenomatous Polyposis Coli (APC), Slimb/βTrCP and SkpA.

In an embodiment of the invention, the ability of an agent to modulate the activity of an activated signaling pathway relative to the control agent is determined by measuring expression of a reporter gene in the plurality of cells, wherein the reporter gene is an exogenous reporter gene responsive to the activated signaling pathway.

In an aspect of the invention, a two-fold or greater decrease or increase in reporter gene expression in the presence of an agent relative to that of the control agent identifies the agent as a modulator of the activated signaling pathway. In a more particular aspect of the invention, a two-fold or greater decrease in reporter gene expression in the presence of an agent relative to that of the control agent identifies the agent as an inhibitor of the activated signaling pathway. In another particular aspect of the invention, a two-fold or greater increase in reporter gene expression in the presence of an agent relative to that of the control agent identifies the agent as an activator of the activated signaling pathway.

In a further aspect, the invention provides a method of treating a mammal susceptible to or afflicted with a condition from among those listed herein, and particularly, such condition as may be associated with e.g., altered Wnt/wg pathway signaling. Such conditions include, without limitation, a variety of hyperproliferative disorders and cancers, including hepatic, colorectal, breast and skin cancers. Additional support for this aspect of the invention is presented in the fact that most cancers of the skin, intestine, and breast epithelial tissue are a result of increased levels of the activated/signaling pool of β-catenin. Since the screen was designed, at least in part, to specifically identify compounds that inhibit the signaling function of β-catenin, it is reasonable to expect that such compounds can be used advantageously to treat such cancers without impairing the normal function/requirement of β-catenin function. Along these lines, evidence from the β-catenin conditional knockout mouse suggests that the normal function/requirement (i.e., adhesion function) of β-catenin in normal cells can be rescued by plakoglobin (γ-catenin). A number of birth defects are also associated with altered Wnt/wg pathway signaling, including debilitating abnormalities of the central nervous system, axial skeleton, limbs, and occasionally other organs.

Other objects and advantages will become apparent to those skilled in the art from a consideration of the ensuing detailed description which proceeds with reference to the following illustrative drawings.

DETAILED DESCRIPTION OF THE INVENTION

Figure 1:
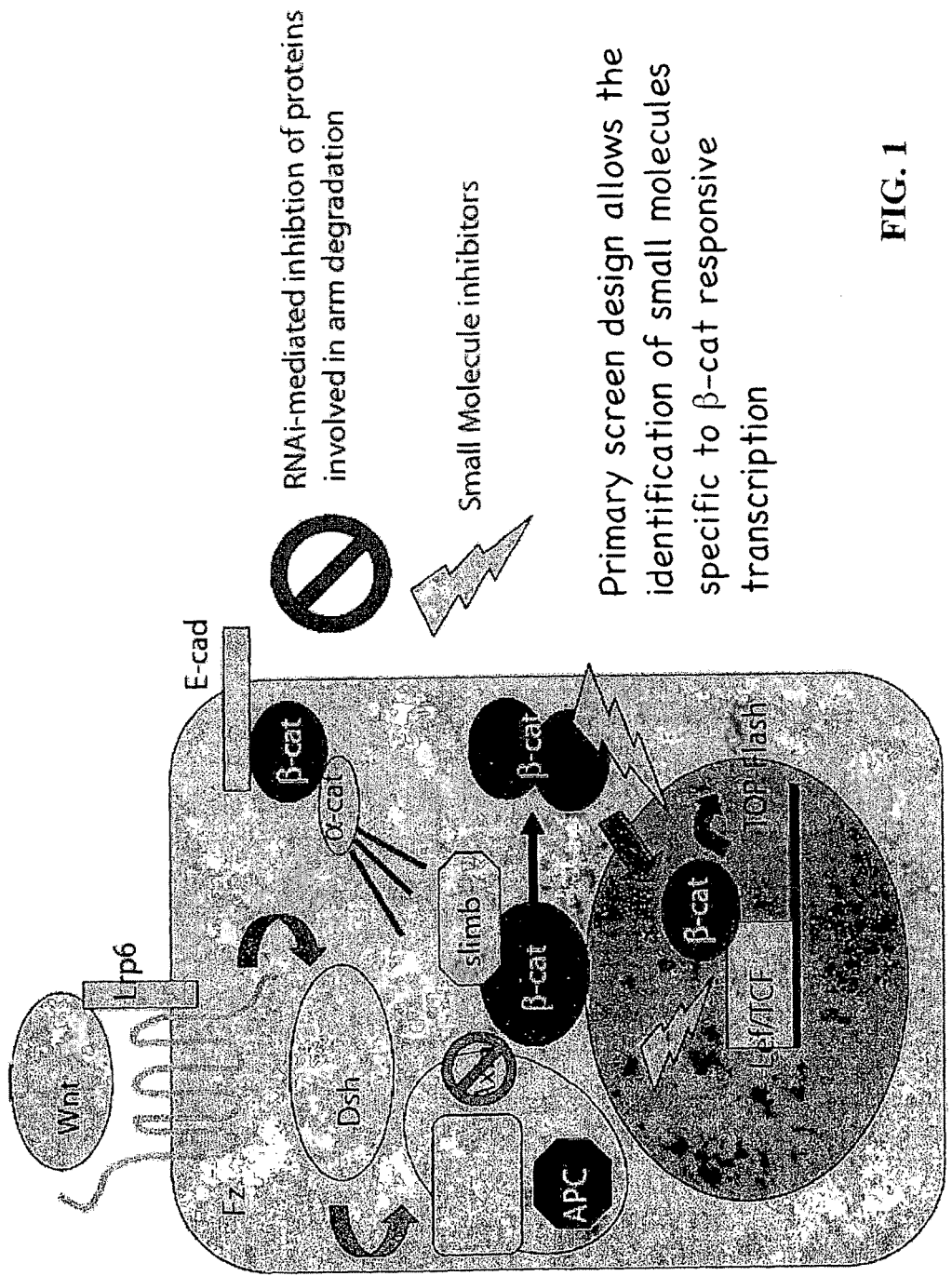
FIG. 1 shows a diagram depicting the Wnt signaling pathway and the rationale for designing a chemical genetic high throuphput screen that specifically targets the activity of stabilized β-catenin.

The present method is particularly well suited to applications wherein a signaling pathway is evolutionarily conserved among Drosophila and mammalian species. Drosophila cells provide an ideal model system in which to screen and identify small molecule modulators that may prove to be effective in mammalian cells because, among other reasons, Drosophila cells share many cellular receptors and signaling pathways in common with mammalian cells. Indeed, the existence of conserved cellular receptors and signaling pathways in Drosophila has presented this genetically-tractable species as representative of higher order eukaryotic cells in many respects. In choosing to analyze a conserved signaling pathway, the screening method of the invention can be performed in Drosophila cells, but the agents identified in such a screen are anticipated to exhibit conserved activity in mammalian cells since they are modulating conserved targets in this cellular milieu. Indeed, the results presented herein demonstrate that agents identified as modulators of the Wnt/wg signaling pathway in Drosophila cells act in a functionally analogous fashion in mammalian cells, thus validating the applicability of the present screening method with regard to identifying potential therapeutics.

The present method may be used to advantage in conjunction with other exemplary evolutionarily conserved signaling pathways, including: the Sonic Hedgehog (SHH) pathway, Epidermal Growth Factor Receptor (EGFR)/Receptor Tyrosine Kinase (RTK) pathway, Notch pathway, Transforming Growth Factor (TGF-β)/Decepentaplegic (Dpp) pathway and the Janus Kinase/Signal Transducers and Activator of Transcription (JAKISTAT) signaling pathway. Indeed, screens for candidate compound modulators (inhibitors and activators) specific for different signaling pathways may be performed for essentially all known signaling pathways in Drosophila and mammalian cells using the specific cell-based assays of the present invention. In order to investigate a candidate molecule's effect on the (SHH)-signaling pathway, a patched-luciferase (PTC-Luci) reporter gene may be used; for the JAK/STAT pathway, a 10x-STAT-luciferase reporter gene may be used; for the Notch pathway, a Hes1-luciferase reporter gene may be used; for the ERK/MAPK pathway, the effect of small molecules on ERK phosphorylation may be monitored using phospho-ERK antibody upon stimulation of cells with secreted EGF ligands such as Spitz; for Insulin/Akt pathway, phospho-Akt antibody upon insulin stimulation may be used; and finally for the Dpp (Tgf-β) pathway, phospho-MAD antibody may be used to study the effect of small molecules on phosphorylation of MAD and its subsequent nuclear translocation upon stimulation of cells with purified DPP protein.

The present method further capitalizes upon the inherent advantages of using *Drosophila* cells in screening assays to identify small molecules that specifically modulate the activity of a target component in a signaling pathway or components downstream of the target component. Yet another benefit conferred by performing screening assays in a *Drosophila* genetic background stems from the fact that *Drosophila* cells have fewer redundant signaling components and/or fewer redundant signaling pathways than mammalian cells. It is, therefore, possible to perform more directed and specific screens in *Drosophila* cells because there are fewer components in the existent signaling pathways, due to the absence of multiple signaling components having partially or fully redundant activity, and there is a dramatic reduction with respect to whole signaling pathways that are partially or fully redundant in nature. The *Drosophila* genetic background, therefore, offers a simplified version of higher eukaryotic signaling machinery which has fewer components, but remains conserved with regard to the essential biochemical components. This feature enables more precise targeting of the activity of a particular signaling component and, thus, more directed screening assays, which in turn expedites identification of small molecules that specifically target the signaling component in question. Since specificity is critical, especially with respect to potential therapeutic agents, this property confers significant advantages to the present screening method.

As indicated above, use of *Drosophila* cells for the primary screens is beneficial due to the lack of redundant mechanisms or redundant families of genes that are typically associated with the mammalian genome. Moreover, transfection efficiencies and other means of delivery of small RNAs (dsRNA or siRNAs) are much more robust in *Drosophila* cells as compared to mammalian cells. For example, with respect to the *Drosophila* Wg pathway, there is only one Axin (a strong negative regulator which acts as a scaffold protein in the β-cat degradation complex). In mammalian cells there are two Axin genes (Axn-1 and Axn-2) that are functionally redundant. Thus, in order to perform a screening method to identify inhibitors in mammalian cells, a co-knockdown both Axn-1 and Axn-2 would be required to achieve the prerequisite activation of the Wnt pathway. Moreover, the addition of multiple siRNAs often leads to reduced transfection efficiency and thus, reduced sensitivity of the Wnt-reporter. In addition, candidate small molecule inhibitors would be required to bind to/inhibit activity of such functionally redundant gene families in order to have an effect on the signaling readout. Finally, a variety of *Drosophila* cell lines, including primary cells, can simply be bathed with dsRNA (cells incubated with serum-free media containing dsRNA), which results in their uptake by cells with almost 100% efficiency, thus bypassing any need for transfection. This phenomenon (bathing-method) is extremely beneficial and powerful in ensuring uniform knockdown of a desired target gene without having to transfect dsRNAs/siRNAs into cells. Taken together, for the purpose of primary screens, the use of *Drosophila* cells for cell-based assays offers a more robust, and sensitive readout for conserved signaling pathways.

Moreover, use of a dsRNA to target an evolutionarily conserved component in a conserved signaling pathway creates a defined target for subsequent screening steps. In other words, performing a screening assay in the context of such a background focuses the screen on the identification of agents capable of modulating the pathway at the level of the targeted conserved component of the pathway or downstream of the conserved component. Use of a dsRNA to target an evolutionarily conserved negative regulator, for example, in a conserved signaling pathway provides a genetic background against which an agent capable of partially or fully restoring activity of the negative regulator can be identified. Such an agent may act, for example, on an immediate downstream target of the negative regulator to inhibit its activity.

The Wnt/Wingless Signaling Pathway

As indicated above, the Wnt pathway is one of a core set of evolutionarily conserved signaling pathways that regulates many aspects of metazoan development. Misregulation or aberrant regulation of the Wnt pathway can lead to adverse effects as demonstrated by the causal relationship identified between mutations in several components of the pathway and tumorigenesis of the liver, colon, breast and the skin. It is, therefore, crucial to develop and implement new technologies in order to generate molecular tools that may be used to modulate the activity of the Wnt/wg signaling pathway. One of the most important effectors of the Wnt pathway is encoded by β-catenin (β-cat)/armadillo (arm). Induction by Wnt ligands leads to stabilization of cytosolic β-cat, which subsequently translocates into the nucleus to activate target genes that regulate many aspects of cell proliferation, growth, differentiation and death.

Since Catenin Responsive Transcription (CRT) has been implicated in the genesis of many cancers, this effector step of the pathway provides a good target for developing therapeutics that could modulate Wnt pathway activity, and more particularly, the nuclear activity of β-cat. The complex regulation of the Wnt/wg pathway at the membrane, however, coupled with the fact that there are several canonical/non-canonical branches of the Wnt pathway, creates a challenging set of obstacles that render it difficult to achieve specificity when designing screens to isolate specific small molecule inhibitors of CRT. It is, therefore, imperative to design assays that would specifically target the active pool of stabilized β-cat upon induction, without affecting the upstream components of the Wnt pathway. The novel screening methods of the present invention address this need and are used herein to identify compounds that specifically target the nuclear activity of β-cat.

The compounds identified using the method of the present invention differ in several aspects from those previously identified as inhibitors of the Wnt pathway. Specifically, the present compounds are not structurally similar to the compounds identified in other screens. Moreover, previously recognized inhibitors were identified using biochemical immuno-enzymatic assays performed in vitro using bacterial expressed GST-tagged proteins. While the compounds were shown to prevent β-catenin/Tcf complex formation, such an approach does not account for all the modifications that these proteins undergo in the context of a cell (in vivo) and may not be prove relevant in a physiological context. They may, indeed, be general inhibitors of β-catenin-mediated protein interactions and thus affect other properties/functions of β-catenin instead of being specific inhibitors of signaling function. Notably, several different families of compounds identified herein are inhibitors that specifically target the activity of the signaling pool of β-catenin. This common functional feature of the instant compounds was an objective of the novel RNAi-chemical genetic screening approach described herein, which is specifically tailored to identify compounds that inhibit the activity of the signaling pool of β-catenin. Moreover, the primary screen and all secondary assays have been performed in vivo in a variety of Wnt-responsive cell types, including fly, human HEK293, mouse breast epithelial C57 mg cells, human breast carcinoma MCF7 cell lines and two different human colon cancer lines, namely HT29 and HT116 cells. One of the strengths of the approach described herein is the specificity built into the screen design and the fact that it was performed in a physiological context.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

As used herein, an "agent", "candidate compound", or "test compound" may be used to refer to, for example, small molecules, nucleic acids (e.g., DNA and RNA), carbohydrates, lipids, proteins, peptides, peptidomimetics, and other drugs.

The term "control substance", "control agent", or "control compound" as used herein refers a molecule that is inert or has no activity relating to an ability to modulate a biological activity. With respect to the present invention, such control substances are inert with respect to an ability to modulate an activated signaling pathway or an RNAi-mediated phenotype in vitro. Exemplary controls include, but are not limited to, solutions comprising physiological salt concentrations.

As used herein, the term "conserved signaling pathway" refers to cell-signaling cassettes or pathways comprising a cascade of genes that are involved in the transduction of a conserved signaling molecule received at the plasma membrane, through the cytoplasm that eventually activate target genes in the nucleus specific to the signaling pathway.

As used herein, the term "conserved component of signaling pathway" refers to genes that are conserved through evolution and play functionally conserved roles in the modulation of a specific signaling pathway. Ideally, a conserved homologue should be able to "rescue" the mutant phenotype of its homolog in another species.

As used herein, the terms "downstream" or "upstream" with respect to a signaling pathway is based on epistatic relationships in a linear signaling cascade: if "A" activates "B" and "B" activates "C", the "A" is upstream of "B" and "B" is upstream of "C". Similarly, "B" is downstream of "A" and "C" is downstream of "B".

As used herein, the term "negative regulator of a signaling pathway" refers to a component of a signaling pathway that inhibits or blocks the pathway. Knockdown of a negative regulator, therefore, activates the pathway, whereas overexpression of a negative regulator inhibits the pathway activity.

As used herein, the term "positive regulator of a signaling pathway" refers to a component of a signaling pathway that promotes or enhances the pathway signaling. Knockdown of a positive regulator, therefore, inhibits (or fails to activate) the pathway, whereas overexpression activates or enhances pathway activity).

As used herein, the term "activates the signaling pathway" refers to a signaling pathway wherein signaling is enhanced or released from negative inhibitory signals.

In certain aspects, the present invention provides prodrugs and derivatives of the compounds that may be developed in accordance with the invention. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as pharmaceuticals, the agents or compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

METHODS OF TREATMENT

The present compounds are used as therapeutic agents for the treatment of conditions in mammals that are causally related or attributable to aberrant activity of the Wnt/wg signaling pathway. Accordingly, compounds that are identified as inhibitors of the Wnt/wg signaling pathway and pharmaceutical compositions thereof find use as therapeutics for preventing and/or treating a variety of cancers and hyperproliferative conditions in mammals, including humans.

In a method of treatment aspect, this invention provides a method of treating a mammal susceptible to or afflicted with a condition associated with cancer and/or a hyperproliferative disorder, which method comprises administering an effective amount of one or more of the pharmaceutical compositions just described.

In yet another method of treatment aspect, this invention provides a method of treating a mammal susceptible to or afflicted with a condition that gives rise to increased cellular proliferation or a transformed phenotype, or that relates to dysregulation of Wnt/wg signaling. The present inhibitor compounds have use as anti-proliferative agents that reduce proliferative levels (potentially to normal levels for a particular cell type), and/or anti-transformed phenotype agents that restore, at least in part, normal phenotypic properties of a particular cell type. Accordingly, the present inhibitor compounds have use for the treatment of cancers and hyperproliferative disorders relating to aberrant Wnt/wg signaling.

In additional method of treatment aspects, this invention provides methods of treating a mammal susceptible to or afflicted with a cancer causally related or attributable to aberrant activity of the Wnt/wg signaling pathway. Such cancers include, without limitation, those of the liver, colon, rectum, breast and skin. Such methods comprise administering an effective condition-treating or condition-preventing amount of one or more of the pharmaceutical compositions just described.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as psoriasis, the regimen for treatment usually stretches over many months or years so oral dosing is preferred for patient convenience and tolerance. Psoriasis, for example, has been linked to Wnt signaling. Several basic and clinical studies using patient samples revealed an increase in nuclear β-catenin staining in many psoriatic samples. It has been suggested that a sustained low-level increase in Wnt/β-catenin signaling could be responsible for skin psoriatic lesions. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of a hyperproliferative condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and that are determined to safe and efficacious for such combined administration.

Example 1

Protocols/Methods for in Vitro Testing

The present inventors employed a novel methodology that integrates a "sensitized" chemical genetic high-throughput screen (HTS) with RNA-interference (RNAi) screening technology in order to identify specific small molecule inhibitors of the Wnt pathway in *Drosophila* cells (FIG. 1). As described herein, *Drosophila* Clone 8 cell-based assay systems developed by the present inventors to investigate the Wnt/wg pathway [DasGupta et al. Science 308, 826-33 (2005)] were used in a small molecule chemical genetic screen to identify specific inhibitors of the pathway. These cell-based assays, which are described in detail below, utilize a Wnt-responsive luciferase reporter dTF12, the activity of which can be determined using immunofluorescence-based visual detection means. The present inventors used the small-molecule library available from the Institute of Chemistry and Cellular Biology (ICCB-Longwood) at Harvard Medical School, Boston, for the screen.

The novelty of the primary screen lies, at least in part, in the combination of the use of RNAi technology and small molecule screening in a single screen to identify novel compounds that modulate the activity of a particular component of a signaling pathway. More particularly, the novel method utilizes a combination of RNAi technology and small molecule screening to identify novel targets that regulate CRT and hence the canonical Wnt pathway. In an embodiment of the invention, the signaling pathway is activated by the introduction of dsRNAs specific for Axin, which is the scaffold protein that negatively regulates β-cat by promoting its GSK-3β-mediated degradation (FIG. 1). The resultant activation of the Wnt signaling pathway is detected by assessing the activity of the Wnt-responsive luciferase reporter gene in the cell-based assay system. Thereafter, small molecules/compounds are added to the cell-based assay system to assess their effect on the strongly induced Wg-reporter-gene (TOPFlash) activity that results from the dsRNA-mediated knockdown of Axin. This protocol significantly increases the specificity of the small-molecule inhibitors for CRT and serves to identify molecules that regulate Wnt signaling activity downstream of the Axin-mediated degradation complex. Although not wishing to be bound by theory, the prediction is that the candidate compounds act on the "activated" or stable pool of β-cat and potentially prevent its interaction with known components of the transcriptional-activator complex (such as pangolin (pan)/dTcf, pygopus (pygo), legless (lgs) or Bcl9, p300/CBP), or other proteins that may function to regulate the activity of stabilized cytosolic β-cat.

Methods and Materials

Primary Small Molecule Screen for the Wingless Signaling Pathway in *Drosophila* Clone 8 Cells Day 1 (PM):

Set up transfection with Wg-reporter (dTF12), Normalization vector (PolIII-RL) and dsRNA against DAxin (dsRNA is specific towards *Drosophila* Axin and lacks any predicted off-targets).

1. Add 40,000 *Drosophila* Clone 8 cells (in 40 μL) in 384-well plate (white solid bottom, Corning Costar) using the multidrop.
2. Add 20 μL of Transfection mix in each well of a 384-well plate (Corning Costar) using the multidrop.

Transfection Mix:

TOP12x-Luc (DNA)=25 ng (0.254 μL of DNA @ 0.1 μg/μL)
PolIII-RLuc (DNA)=25 ng (0.25 μL of DNA @ 0.1 μg/μL)
dsRNA to DAxin=100 ng (54 of dsRNA @ 20 ng/μL)
Buffer EC=13.5 μL
Enhancer=0.8 μL
Effectene=0.25 μL
Total volume=20 μL Incubate at 25° C. for 4 days to ensure complete knockdown of Axin.

Day 5 (PM):

Add small molecule library (Cybio Robot). Incubate 18 hrs.

Day 6 (AM):

Assay luminescence from the samples using the "Dual-Glo" luciferase kit (Promega Inc.). Specifically, aspirate supernatant and add 20 μL media+20 μL luciferase buffer using the multidrop. Read Firefly Luciferase activity on the En Vision (Perkin Elmer plate reader). Add 20 μL of Stop&Glo using the multidrop. Read Renilla luciferase activity on the En Vision (Perkin Elmer plate reader).

Epistasis Analysis: Epistasis Analysis was conducted in a 96 well format following the protocol as described for the Primary Screen (above), except that, 80,000 Clone 8 cells were used per well. Small Molecule Compounds were used at a final concentration of 2.5 ng/ul.

Reporter Assay in Mammalian HEK 293 cells: HEK 293 cells were transfected with 50 ng each of the Wnt-responsive STF16 luciferase reporter and pCMV-RL normalization reporter using the Lipofectamine LTX (Invitrogen Inc.) in a 96 well plate format.

Transfection Mix Per well

STF16-FLuc (DNA): 50 ng (0.5 μL of DNA @ 0.1 μg/μL)
CMV-RLuc (DNA): 50 ng (0.5 μL of DNA @ 0.1 μg/μL)
Lipofectamine-LTX: 0.25 μL
Serum Free Medium: 20 μL Cells were cultured in DMEM/10% FBS at 37° C. for 2 days following which, they were induced with Wnt3a conditioned media for 1 day and then treated with small molecule compounds to a final concentration of 2.5 ng/μl for approximately 18 hours. Luciferase reporter activity was then measured using the Dual-Glo system (Promega Inc.) on the Envision Plate Reader. Normalized luciferase activity in response to treatment with candidate small molecule compounds was compared to that obtained from cells treated with DMSO.

C57 mg transformation Assay: The transformation assay was carried out in a 96 well format. C57 mg cells were cultured in DMEM/10% FBS supplemented with purified Wnt3a protein (R&D Systems) to a final concentration of 100 ng/μl. Small molecule compounds dissolved in DMSO were added to a final concentration of 10 ng/μl and 0.01% DMSO. Following incubation at 37° C. for 5 days, cells were fixed with 4% Formaldehyde in 1×PBS at RT for 30 min and washed subsequently with 1×PBS at room temperature (RT) for 5 minutes (×3). Cells were then permeabilized in Blocking buffer (0.1% Triton-X/1×PBS/5% Normal Goat Serum) at RT for 20 min, subsequent to which, cells were incubated with anti-β-cat at RT for 1 hour (diluted to 1:1000 in blocking buffer). Subsequently, cells were washed with 1×PBS at RT for 10 minutes (×3) and then incubated with secondary antibody and Alexa-Fluor 488 conjugated phalloidin in Blocking buffer at RT for 1 hour. Following a brief wash in 1×PBS, cells were imaged in PBS buffer using the Array-Scan imaging system.

Molecular validation of C57 mg transformation assay was performed by qPCR analysis of the Wnt-target gene, WISP1. First strand cDNA was prepared from C57 mg cells treated as above using Cells-to-cDNA kit (Ambion, Inc.) as directed by the manufacturer. Equal amounts of cDNA were used for qPCR analysis using primers specific for WISP1 and GAPDH (the endogenous control). Comparison of amplification kinetics of WISP1 from samples treated with compounds to those treated with DMSO (ddCt method) was used to study changes in Wnt-directed transcriptional activity in response to treatment with candidate small molecule compounds.

Unless otherwise indicated, all experiments described herein that call for supplemental Wnt3a utilize Wnt3a conditioned media prepared by harvesting media from L-cells stably transfected with a Wnt3a coding construct (available from ATCC #CRL-2647). The cells are cultured in DMEM containing 10% fetal bovine serum (FBS). The medium, harvested from adherent cells cultured to about 80% confluency over 4 days, is purified through a 0.2 μm filter and stored at 4° C. over several months without an appreciable loss in activity [Willert et al. Nature 423, 448-52 (2003)].

Results

Clone 8 cells were used for the present assay because the Wg-responsive luciferase reporter-gene (dTF12) is extremely sensitive in these cells. This is evidenced by the finding that the present inventors observe a 30-40 fold induction in a 384-well plate format upon dsRNA-mediated knockdown of Axin which can then be easily modified by the addition of relevant candidate inhibitors.

Figure 2:
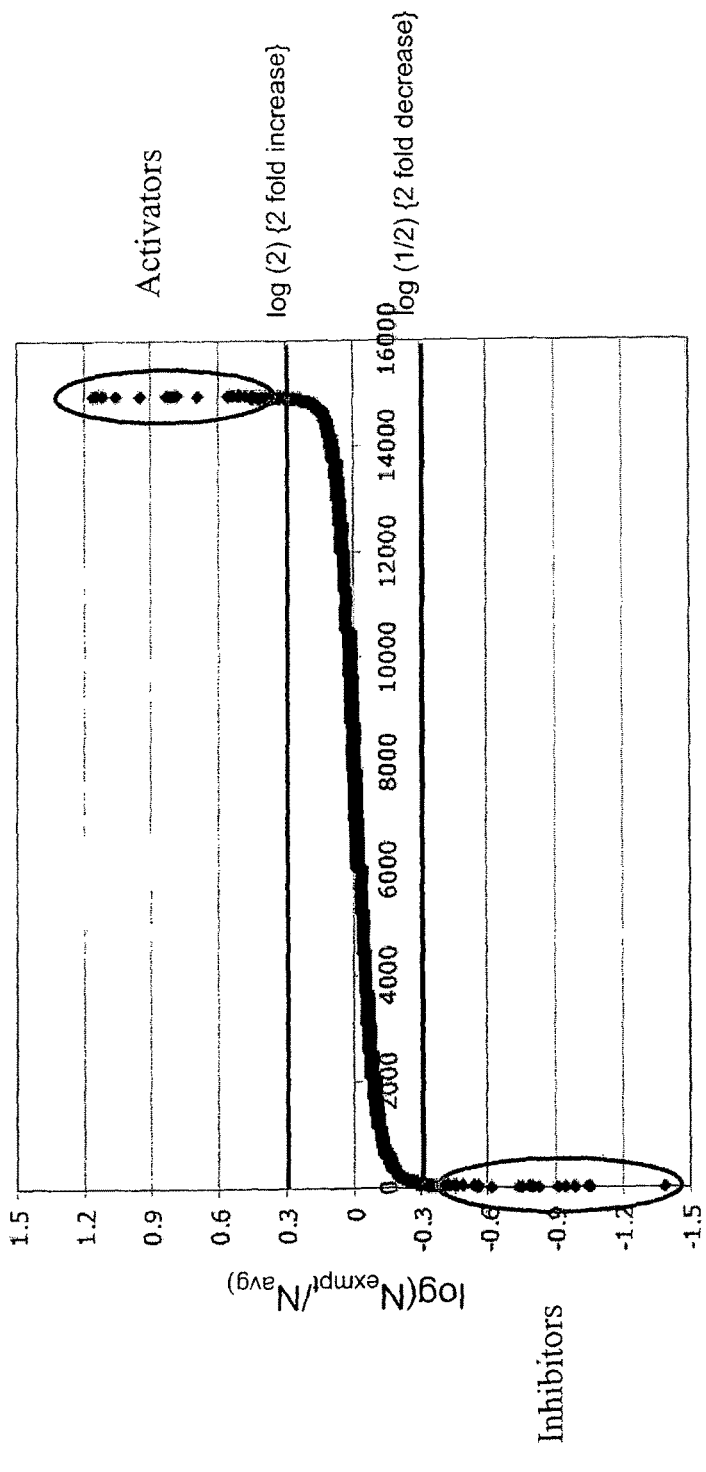
FIG. 2 is a graphical representation of the small molecule primary screen with "normalized luciferase activity" shown on the y-axis.
Figure 3:
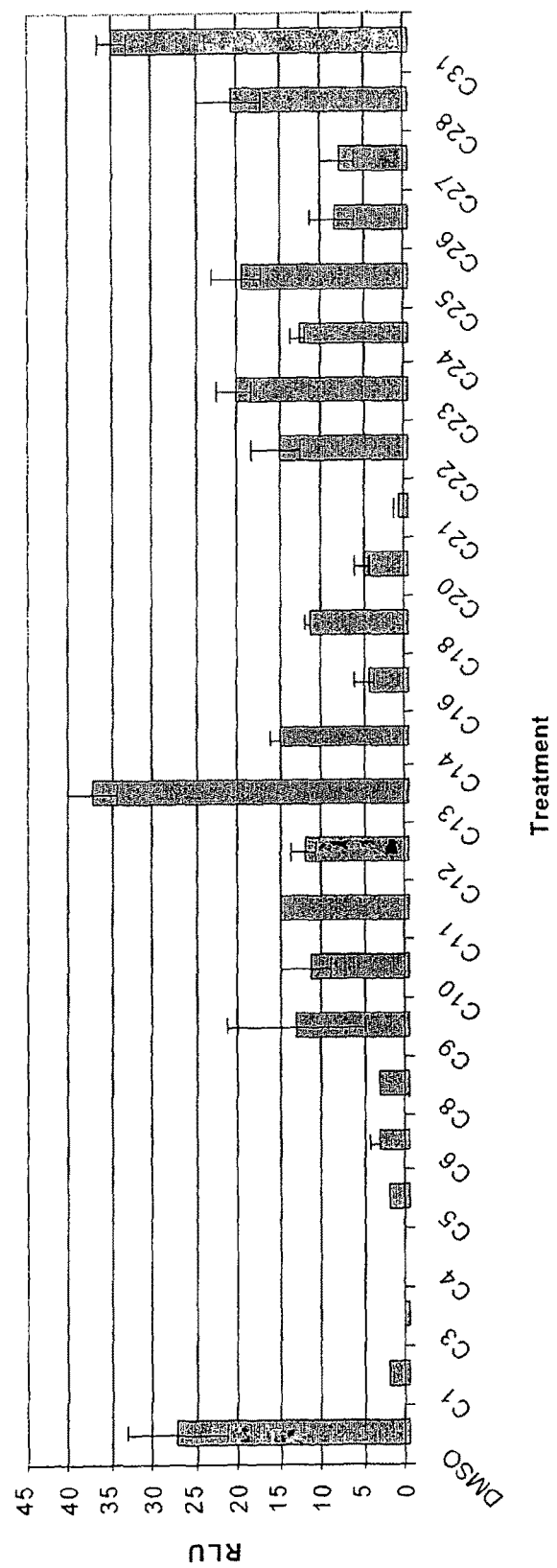
FIG. 3 shows a bar graph depicting the activity of candidate inhibitors on TOP12-LF in Clone 8 cells.

The Wnt signaling pathway was induced by the introduction of dsRNAs specific for Axin into Clone 8 cells comprising the Wg-responsive luciferase reporter-gene (dTF12). As described herein, Axin is a scaffold protein that negatively regulates Arm/β-cat by promoting its degradation. Thereafter, a selected set of a small molecule library was added to the Clone 8 cell-based assay system to assess the effect of individual compounds on (Axin dsRNA-mediated) activated CRT by monitoring the activity of the Wg-responsive luciferase reporter-gene (dTF12). The present inventors screened 14,977 compounds to assess their effect on the modulation of Wnt/wg reporter activity/CRT. See FIG. 2. As shown in FIG. 2, addition of most compounds did not affect Wnt-reporter activity. The primary screen did, however, identify 34 molecules that have a statistically significant effect on the activity of the dTF12-luciferase reporter gene, wherein a minimum of a 2.5-fold change in reporter activity was considered "significant" as a cut-off for hit-picking compounds for secondary screens. As shown in FIG. 3, addition of these compounds to the cells strongly repressed dTF12-reporter activity (>70-90%). Six of the strongest inhibitors are identified herein and, as indicated, share significant structural similarities suggesting that they constitute a family of compounds (i.e., a subset of oxazoles) that regulate a common aspect of the Wnt-pathway activity by potentially binding to the same target protein.

Figure 4:
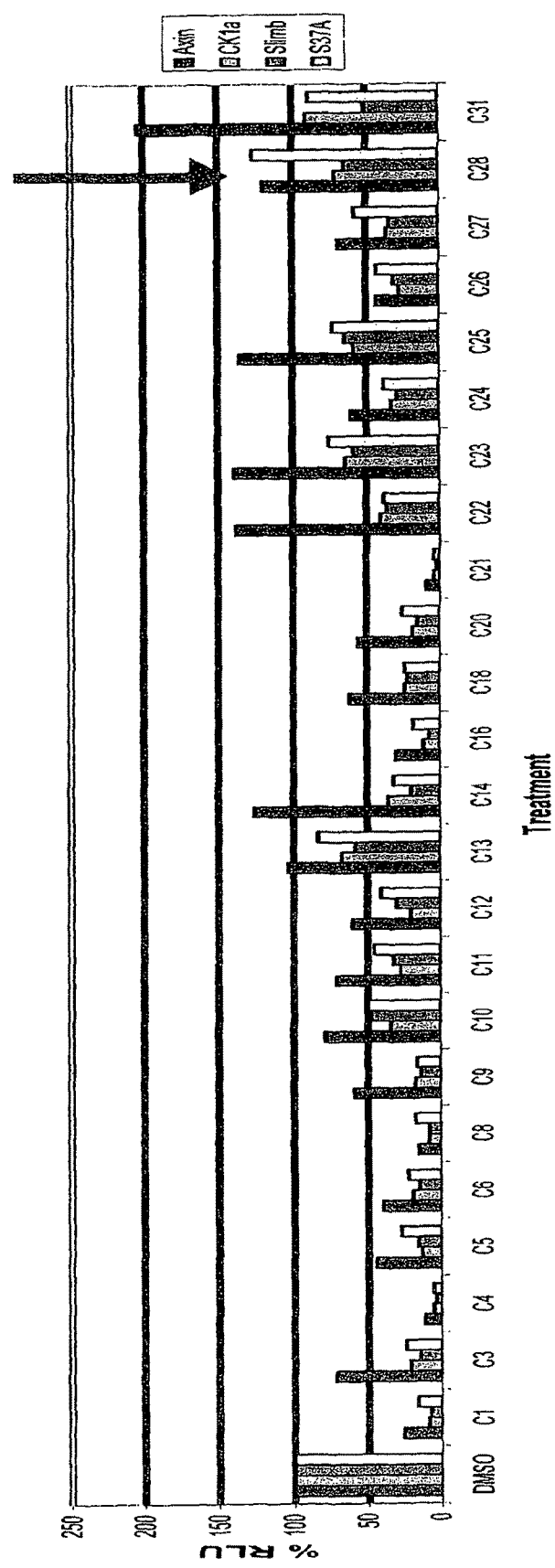
FIG. 4 shows a bar graph depicting the results of genetic epistasis analyses.

Epistasis Analyses: Small molecule inhibitors identified in the primary screen may modulate Wnt signaling by affecting intermolecular interactions at any point downstream of Axin in the signaling cascade. Given that the oncogenic character of β-cat and therefore the Wnt pathway itself is caused by aberrant CRT (Park et al. Cancer Res 59, 4257-60 (1999); Lin et al. Proc Natl Acad Sci USA 97, 4262-6 (2000), a major focus of the present invention is to study those compounds which affect Wnt-responsiveness by regulating the transcriptional complex involved in CRT. The use of dsRNAs targeted to specific components of the Wnt pathway elucidates the level at which the compounds exert their inhibitory effect on the Wnt/Wg signaling pathway. This objective can be achieved by activating the Wnt pathway in Clone 8 cells using dsRNAs targeting other known negative regulators of the Wnt pathway, such as Slimb/βTrCP and SkpA, and assaying the effect of the compounds on the dTF12 reporter activity in these cells. Each of the aforementioned biomolecules functions to negatively regulate Wnt signaling downstream of Axin, so these analyses further delineate the stage in the Wnt pathway wherein the compound in question exerts its effect. See FIG. 1 for diagram of the epistatic relationship of these components of the Wnt pathway. Results of such an experimental approach are presented in FIG. 4.

Figure 5:
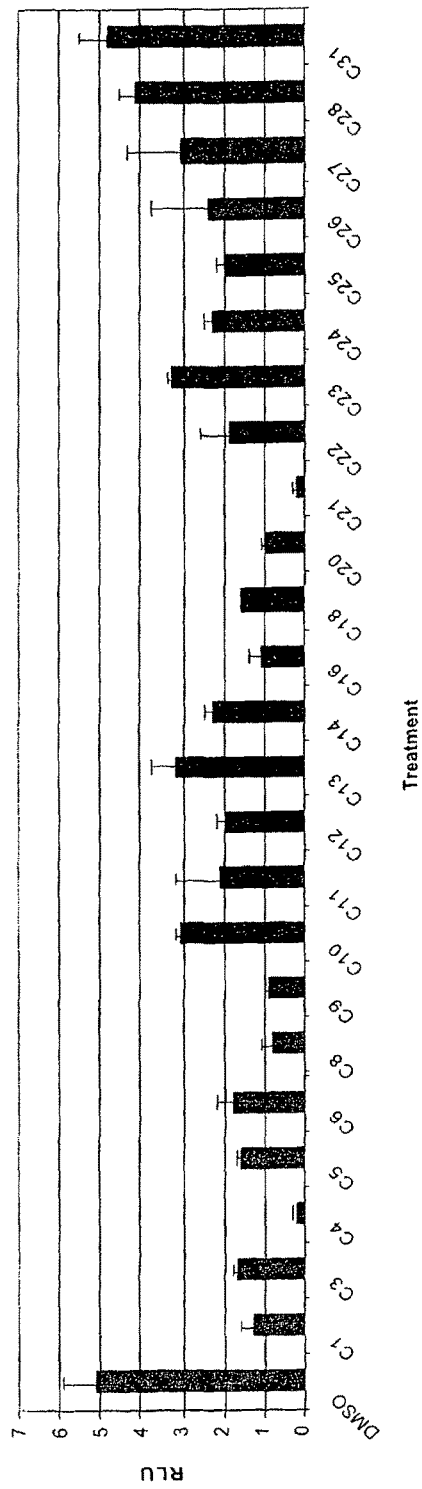
FIG. 5 shows a bar graph depicting the activity of candidate inhibitors on S37A β-catenin mediated TOP12-LF in Clone 8 cells.

To gain further evidence that the compounds exert their inhibitory effect in the nucleus, they have been tested in Clone 8 cells transfected with a construct coding for a degradation resistant form of β-cat, S37A β-cat [Orford et al. J Biol Chem 272, 24735-8 (1997)]. This mutant form of β-cat bears a Serine to Alanine mutation, thus rendering it refractory to GSK3β mediated phosphorylation and hence proteosome degradation. An inhibitory effect of the compounds on the activity of S37A β-cat thus provides further proof that the compounds exert their effect on Wnt responsiveness at the level of CRT. The concentration of the compounds for all of the above assays is kept constant at 2.5 ng/μl, which is the same as that used for the primary screen. As shown in FIG. 5, most of the compounds exert an inhibitory effect on Wnt signaling on the transcriptional level. Data depicted in FIG. 5 show that a majority of the compounds inhibit S37A-mediated reporter activity, thus lending further support to the notion that these putative inhibitors do indeed function by abrogating the activity of stabilized β-cat in the nucleus.

Figure 6:
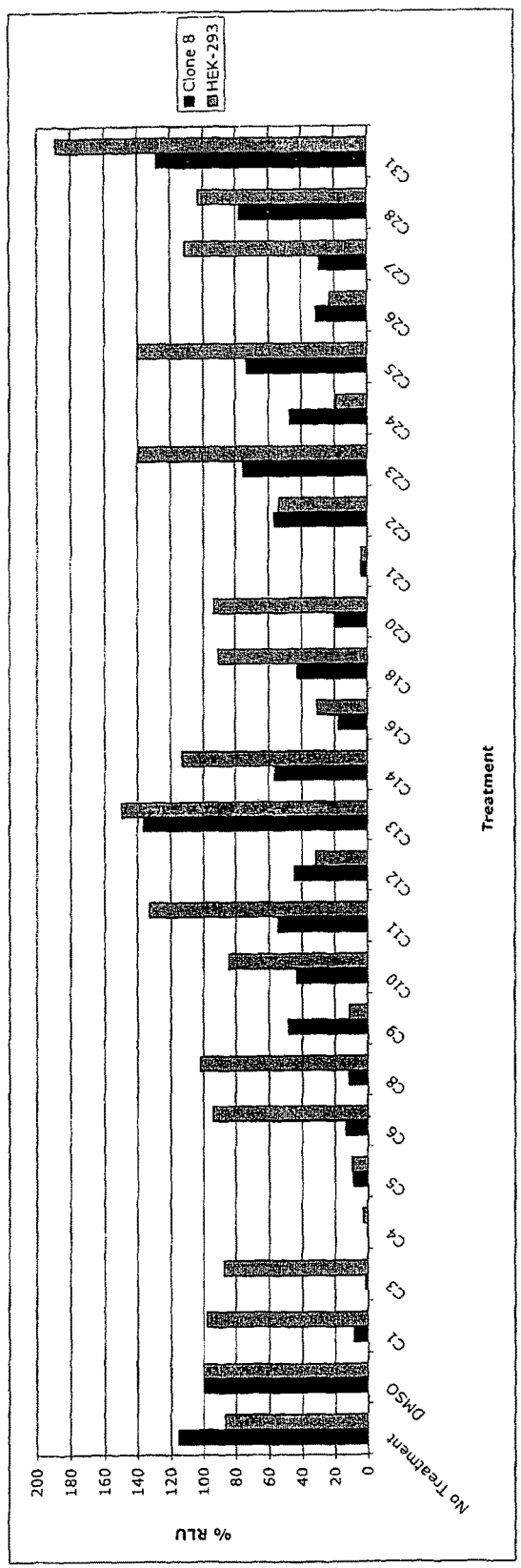
FIG. 6 shows a bar graph representation of the effect of several inhibitory compounds in mammalian HEK-293 cells.

Reproducibility of inhibitory effect of small molecules in mammalian cells: In order to confirm and corroborate the activity of CRT inhibitor compounds in a mammalian context, the present inventors have tested a subset of the inhibitors identified in the context of established mammalian cell lines. To this end, the present inventors have optimized culture conditions for screening for Wnt signaling modulators in mammalian HEK 293 cells in a 96-well plate format. Briefly, HEK 293 cells were transfected with pSTF16-LF along with the normalization reporter, pCMV-RL and the effect of the compounds on reporter activity in such cells was determined by quantifying the luminescence from the luciferase reporter gene as described in Dasgupta et al. [supra (2005)]. As shown in FIG. 6, the present inventors have been able to recapitulate the inhibitory effect of several candidate inhibitors in these cells using the Wnt responsive luciferase reporter, STF16-LF.

In that Wnt signaling has been shown to have a profound influence on both cell fate and cell proliferation in various developmental and pathogenic contexts [Clevers. Cell 127, 469-80 (2006)], the present inventors have begun to investigate the activity of a subset of the CRT inhibitors identified in the primary screen in the context of other available Wnt responsive cell lines. Such cell lines can be used to ascertain further the inhibitory activity of the putative small molecule inhibitors in a phenotypic context. Such Wnt responsive cell-specific phenotypes include an assessment of transformation of the C57 mg mammary epithelial cell line, neural differentiation capacity of G-Olig2 ES cells, E-cadherin expression in the HT-29 colon cancer cell line, and Wnt induced invasive capacity of the MCF-7 breast adenocarcinoma cell line.

The C57 mg cell line, which was isolated from mouse mammary epithelial tissue [Wong et al. Mol Cell Biol 14, 6278-86 (1994)], has previously been shown to undergo transformation when cultured in Wnt-conditioned media. Transformation of the cell line is evidenced by pronounced changes in morphology, typified by formation of chord-like bundles of cells or foci-forming colonies that break off and float in the media [Wong et al. supra, 1994]. This Wnt responsive phenotype provides a mammalian assay in which to evaluate the inhibitory effect of the small molecule inhibitors identified in the primary screen. Briefly, cells are cultured in Wnt3a conditioned media in the presence or absence of a small molecule inhibitor and morphological analysis conducted using automated microscopy.

Figure 7:
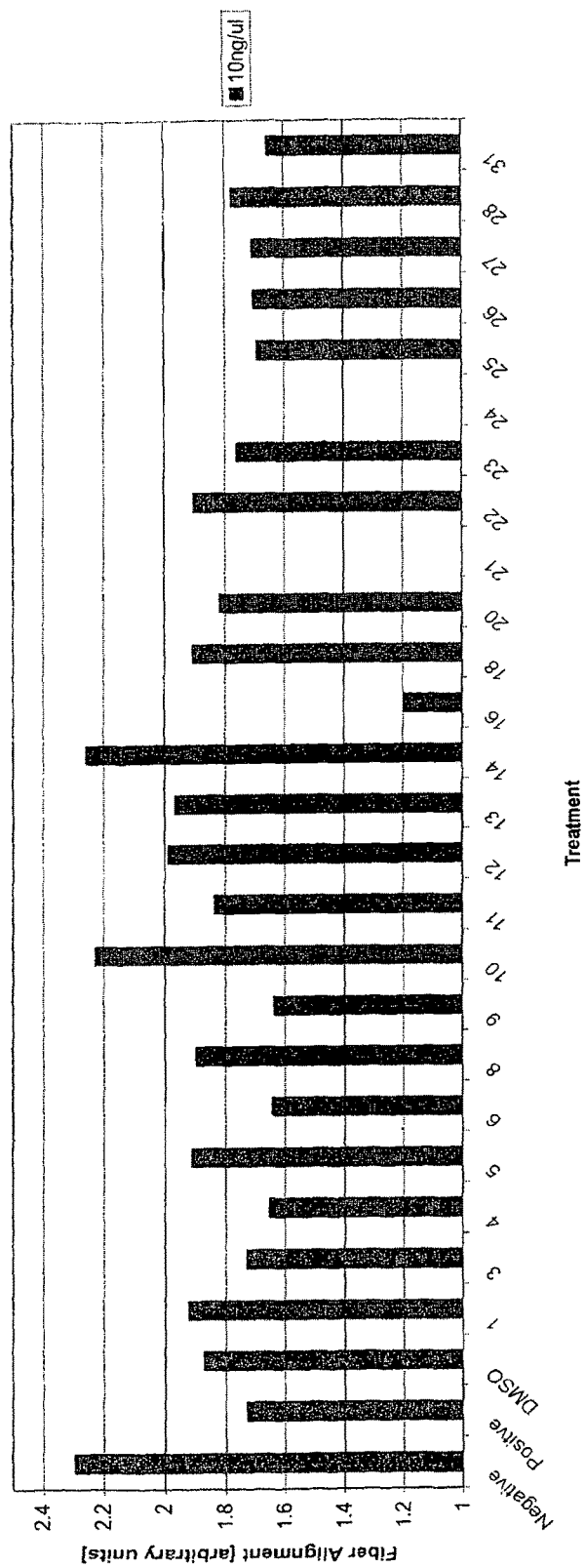
FIG. 7 shows a bar graph of quantitative analyses of Wnt3a transformed C57 mg cell phenotypes and rescue thereof by inhibitory compounds.

The present inventors have established a phenotypic assay using the Wnt-responsive C57 mg mouse mammary epithelial cell line to ascertain the validity of the inhibitory compounds identified in the primary screen. Specifically, addition of Wnt3a conditioned media or purified Wnt3a protein results in cellular transformation, manifested by a pronounced change from an epithelial-cell like morphology to those resembling spindle shaped cells with chord like bundles. Addition of candidate small molecule compounds to such cells in the presence of Wnt3a results in significant inhibition of the transformation phenotype. The Array-Scan imaging system (Cellomics Inc.) is used to image such phenotypic changes in a 96-well plate format so as to gain a quantitative estimate of the degree of the inhibitory effect of the compounds on Wnt3a induced transformation in C57 mg cells. Quantitative analysis of the transformation phenotype is measured by the degree of actin fiber alignment (defined as anisotropy), which is expressed as the standard deviation (SD) of the angles projected by the actin fibers relative to the normal; low SD numbers reflect an increase in Wnt-responsive transformation. This approach allows for objective inferences on the cellular effects of the candidate inhibitors. See FIG. 7. As depicted in FIG. 7, compounds 10 and 14 show a significant inhibition of Wnt3a induced C57 mg transformation, whereas compounds 1, 5, 8, 11, 12, 13, 18 and 22 show a partial reduction in the degree of transformation. It should be noted that the degree of inhibitory effect of the compounds on Wnt-induced phenotypes may vary with different cellular types. For example, compounds 10 and 14 are poor inhibitors of TOP12-LF activity in HEK-293 cells (see FIG. 6), and yet seem to be potent inhibitors of Wnt3a-induced transformation in C57 mg cells.

Figure 8:
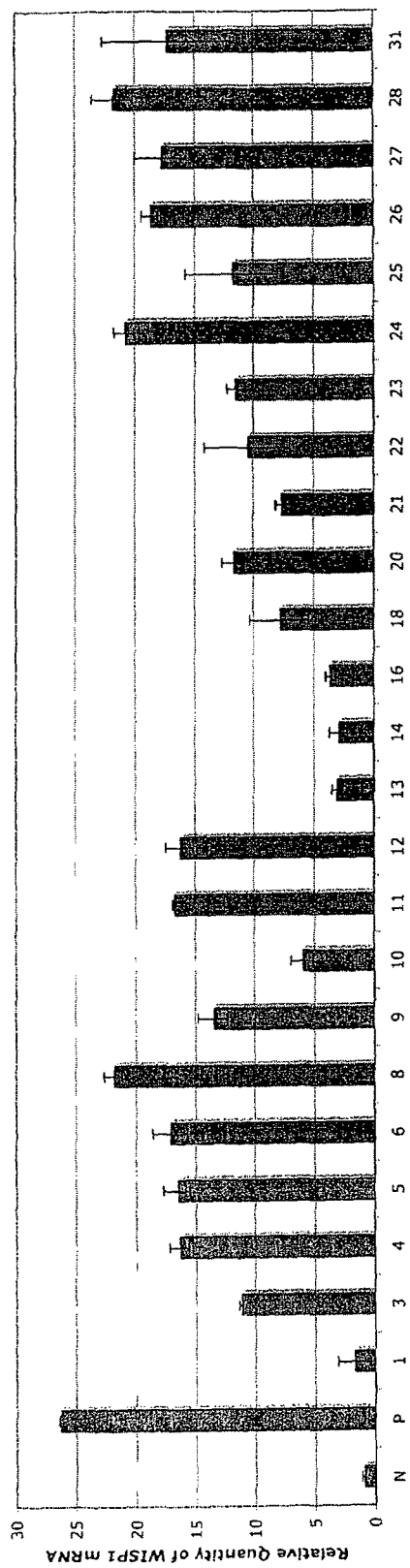
FIG. 8 shows a bar graph revealing changes in the expression of WISP1 mRNA in Wnt3a transformed C57 mg cells responsive to inhibitory compounds.

This could perhaps be due to their effect on the interaction of β-cat with different transcriptional co-factors in the nucleus that drive transcription of different targets. To further validate the efficacy of candidate compounds in inhibiting Wnt-induced C57 mg transformation, the present inventors monitored changes in the expression of WISP1 mRNA by qRT-PCR. WISP1 is the key β-catenin target responsible for C57 mg transformation in response to Wnt signaling [Xu et al. Genes Dev. 14, 585-95 (2000)]. Reduction in the level of WISP1 mRNA correlates with the observed phenotypic rescue in response to Wnt exposure (see FIG. 8).

The HT-29 colon cancer cell line has been shown to undergo β-cat/TCF dependent Epithelial Mesenchymal Transition (EMT) which can be monitored by changes in both morphology and downregulation of E-cadherin expression levels and upregulation of vimentin [Yang et al. Cell 127, 139-55 (2006)]. The HT-29 cell line, therefore, provides a model system for analysis of the candidate small molecule inhibitors in the context of a transformed colon cancer cell. Accordingly, the present inventors will treat HT-29 cells with candidate small molecules and assay E-cadherin and vimentin levels by western blotting as well as immunochemistry using commercially available antibodies. Furthermore, morphological analysis by compound differential contrast (DIC) microscopy will also be used to determine the effect of the compounds in inhibiting β-cat dependent EMT.

The MCF-7 breast cancer cell line exhibits a pronounced invasive capacity in response to Wnt signaling [Yook et al. Nat Cell Biol 8, 1398-406 (2006)]. To utilize this cell line to assess the activity of Wnt inhibitor compounds identified, MCF-7 cells can be transduced with recombinant retroviral vectors coding for Wnt3a or β-cat-S33Y, a constitutively active form of β-cat [as described in Yook et al. supra, (2006)]. The retroviral vectors will be prepared from pPGS-β-cateninS33Y- or pPGS-Wnt3a-transfected 293 packaging cells. MCF-7 cells transduced with these retroviral vectors can be loaded onto the upper chamber of Matrigel (prepared in serum-free DMEM culture media) containing Transwells, which are subsequently cultured in complete media with inhibitory compounds or DMSO. The cultures will be incubated at 37° C. in a humidified chamber for 24-72 hrs. Following incubation of the cell-loaded Matrigel, non-invasive cells are scraped off and the invaded cells counted by simple light microscopy by fixing and staining with Trypan Blue [Valster et al. Methods 37, 208-15 (2005)]. Results derived from this assay will provide insights into the use of compounds as inhibitors of the metastatic potential of malignant cells in general and malignant breast cancer cells in particular.

G-Olig2 ES cells (available from ATCC) contain a GFP insertion in the gene for Olig 2, a neural lineage specific transcription factor. Neural differentiation, therefore, results in the upregulation of GFP-positive cells. Neural differentiation of G-Olig2 ES cells can be induced by treating these cells with synthetic Retinoic Acid (RA) following the appearance of Embryoid bodies in culture. It has previously been shown that Wnt signaling inhibits neural differentiation of ES cells [Bouhon et al. Brain Res Bull 68, 62-75 (2005)]. To assay the inhibitory effect of the candidate compounds, the present inventors will culture the above ES cells in Wnt3a conditioned media containing RA and individual compounds and determine the number of GFP positive cells by Flow Cytometry. The inhibitory effect on Wnt signaling will be reflected by a reduction in the number of GFP positive differentiated cells in cultures treated with DMSO+RA as compared to those treated with compound+RA.

Although the present Example is directed to screening in the context of an "activated" Wnt pathway, it will be appreciated that other components of the pathway that promote Wnt signaling can be targeted for RNAi mediated ablation and the result of such an approach would be an "inhibited" Wnt pathway. In either event, the cellular milieu of an "activated" or an "inhibited" Wnt pathway can be used as a genetic background in which to perform small molecule/compound chemical screens directed to the identification of small molecules/compounds that modulate the activity of a specific component of a signaling pathway.

Example 2

Protocols/Methods for In Vitro and In Vivo Testing

Preliminary in vivo tests to assay the efficacy of the compounds will be performed in the zebrafish, *Danio rerio*, wherein increased Wnt signaling during zebrafish embryonic development results in axial specification defects and loss of anterior fates. This is commonly manifested by loss of or reduced eye-structures. To test the effectiveness of the compounds in inhibiting Wnt-signaling in a whole organismal context, one-cell embryos will be injected with synthetic Wnt8 mRNA and cultured in the presence of DMSO or individual compounds. Inhibitory activity of the compounds will be assayed by quantifying the penetrance of the Wnt8 induced phenotype.

Upon successful in vivo validation of the compounds in an animal model system, their efficacy will be further tested in the clinically relevant mouse model system, viz. the $APC_{min}$ mouse. Loss of APC function results in an increase in the level of signaling competent β-catenin, which has been shown to be the causative factor in the induction of colon cancer in the above mouse model. Such mice will be administered candidate compounds and assayed for the regression of tumors resulting from increased Wnt signaling in the $APC_{min}$ mouse. Standardized protocols for tail-vein and/or tissue injections will be used.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

What is claimed is:

1. A method for screening to identify a small molecule agonist or antagonist capable of modulating the activity of an activated signaling pathway in a cell, wherein the activated signaling pathway is the Wnt/wg signaling pathway, the method comprising:
    a) contacting a plurality of cells in vitro with a double-stranded RNA (dsRNA) to induce uptake of the dsRNA into the plurality of cells, wherein the dsRNA is specific for a negative regulator of the signaling pathway, wherein the negative regulator is selected from the group consisting of axin, Glycogen Synthase Kinase-3β (GSK-3β), Adenomatous Polyposis Coli (APC), Slimb/BTrCP and SkpA, and wherein uptake of the dsRNA reduces the activity of the negative regulator and thereby activates the signaling pathway in the plurality of cells; and b) dividing the plurality of cells comprising the activated signaling pathway into isolated subpopulations and incubating each isolated subpopulation in the presence of a small molecule of a small molecule library to determine if the small molecule modulates the activity of the activated signaling pathway relative to a control agent, wherein each subpopulation is incubated with a different small molecule, and wherein an ability to modulate the activity of the activated signaling pathway relative to a control agent identifies the small molecule as a small molecule agonist or antagonist of the signaling pathway in a cell.

2. A method for screening to identify a small molecule agonist or antagonist capable of modulating an RNA-interference (RNAi)-mediated phenotype in a cell, the method comprising:
   a) contacting a plurality of cells in vitro with a double-stranded RNA (dsRNA) to induce uptake of the dsRNA into the plurality of cells, wherein the dsRNA is specific for a negative regulator of a signaling pathway, wherein the negative regulator is selected from the group consisting of axin, Glycogen Synthase Kinase-3β (GSK-3β), Adenomatous Polyposis Coli (APC), Slimb/BTrCP and SkpA, and the signaling pathway is the Wnt/wg signaling pathway and wherein uptake of the dsRNA reduces the activity of the negative regulator, thereby creating an RNAi-mediated phenotype characterized by activation of the signaling pathway in the plurality of cells; and
   b) dividing the plurality of cells having the RNAi-mediated phenotype into isolated subpopulations and incubating each isolated subpopulation in the presence of a small molecule of a small molecule library to determine if the small molecule modulates the RNAi-mediated phenotype relative to a control agent, wherein each isolated subpopulation is incubated with a different small molecule, and wherein an ability to modulate the RNAi-mediated phenotype relative to the control agent identifies the small molecule as a small molecule agonist or antagonist capable of modulating the RNAi-mediated phenotype in a cell.

3. The method of claim 1, wherein the method is a high throughput screen.

4. The method of claim 1, wherein the plurality of cells are *Drosophila* cells.

5. The method of claim 4, wherein the *Drosophila* cells are a *Drosophila* cell line.

6. The method of claim 5, wherein the *Drosophila* cell line is selected from the group consisting of Clone 8 cells or derivatives thereof.

7. The method of claim 1, wherein the ability of the small molecule to modulate the activity of the activated signaling pathway relative to the control agent is determined by measuring expression of a reporter gene in the plurality of cells, wherein the reporter gene is an exogenous reporter gene responsive to the activated signaling pathway.

8. The method of claim 7, wherein a two-fold or greater decrease or increase in reporter gene expression in the presence of the small molecule relative to that of the control agent identifies the small molecule as a modulator of the activated signaling pathway.

9. The method of claim 8, wherein a two-fold or greater decrease in reporter gene expression in the presence of the small molecule relative to that of the control agent identifies the small molecule as an inhibitor of the activated signaling pathway.

10. The method of claim 8, wherein a two-fold or greater increase in reporter gene expression in the presence of the agent relative to that of the control agent identifies the agent as an activator of the activated signaling pathway.

* * * * *